United States Patent
Alfano et al.

[11] Patent Number: 5,949,077
[45] Date of Patent: Sep. 7, 1999

[54] TECHNIQUE FOR IMAGING AN OBJECT IN OR BEHIND A SCATTERING MEDIUM

[76] Inventors: Robert R. Alfano, 3777 Independence Ave., Bronx, N.Y. 10463; Kwong Mow Yoo, 412 W. 148th St. Apt. 2G, New York, N.Y. 10031; Samir Ahmed, 345 E. 81 St. Apt 21B, New York, N.Y. 10028; Zhi-Wei Zang, 611 W. 137 St. Apt. #61, New York, N.Y. 10031; Feng Liu, 3055 Bailey Ave. Apt. E2, Bronx, N.Y. 10463

[21] Appl. No.: 08/189,124

[22] Filed: Jan. 28, 1994

Related U.S. Application Data

[63] Continuation of application No. 07/927,566, Aug. 10, 1992, abandoned.

[51] Int. Cl.$^6$ .................................................. G01N 24/64
[52] U.S. Cl. .................................... 250/459.1; 250/458.1; 250/461.1; 250/461.2
[58] Field of Search ............................. 250/461.2, 461.1, 250/459.1, 458.1

[56] References Cited

U.S. PATENT DOCUMENTS

| | | |
|---|---|---|
| 5,022,757 | 6/1991 | Modell ...................................... 356/318 |
| 5,097,135 | 3/1992 | Makino et al. ........................ 250/461.1 |
| 5,140,463 | 8/1992 | Yoo et al. ................................. 359/559 |

OTHER PUBLICATIONS

Alfano et al., "Photons for prompt tumor detection," Physics World, pp. 37–40 (Jan. 1992).

Wang et al., "Ballistic 2–D Imaging Through Scattering Walls using an Ultrafast Optical Kerr Gate," Science, vol. 253, pp. 769–771 (Aug. 16, 1991).

Yoo et al., "Imaging objects hidden in scattering media using a fluorescence–absorption technique," Optics Letters, vol. 16, No. 16, pp. 1252–1254 (Aug. 15, 1991).

*Primary Examiner*—Constantine Hannaher
*Attorney, Agent, or Firm*—Kriegsman & Kriegsman

[57] ABSTRACT

A technique for forming an image of an object in or behind a scattering medium. In one embodiment, the object is made luminescent, and the luminescent light is selected for imaging while the illuminating light is filtered out. The quality of the image can be further improved by selected the portion of the luminescence spectrum that is strongly absorbed by the scattering medium.

7 Claims, 4 Drawing Sheets

TECHNIQUE FOR IMAGING AN OBJECT IN OR BEHIND A SCATTERING MEDIUM

This is a continuation of application Ser. No. 07/927,566 filed on Aug. 10, 1992, now abandoned.

BACKGROUND OF THE INVENTION

The present invention relates generally to techniques for imaging an object in or behind a scattering medium and more particularly to a novel technique for imaging an object in or behind a scattering medium.

An object embedded in a highly scattering random medium cannot be easily observed because multiple light scattering randomizes the signal light direction. Objects hidden in random scattering media are common in nature, and developing a simple technique to see such hidden objects is important for many fields. In medicine, for example, it is highly desirable to image the tumor hidden in a breast by using light instead of x-rays. An optical imaging method called transillumination or diaphanography has been developed. In this method, light is incident upon the breast, and the transmitted light is measured. A shadow of the tumor may be observed because the absorption and scattering characteristics of the tumor are different from those of the normal tissue. Typically, a tumor of 1-cm diameter can be detected. However, multiple light scattering in the breast blurs the image and may result in making the tumor unrecognizable, especially when the tumor is too small or lies too deep in the breast. Recently, ultrafast laser technology was used to enhance the image by time gating the ballistic component of the laser pulses and eliminating the diffuse pulse from detection. This time-gating technique has been used by various groups to enhance the image of an object hidden in the random medium.

Publications of interest to the present invention include Yoo et al., Optics Letters, Vol. 16, No. 16, 1252–1254 (1991); Andersson-Engels et al., Optics Letters, Vol. 15, No. 21, pp. 1179–1181 (1990); Maarek et al., Medical & Biological Engineering & Computing, pp. 407–414 (July 1986); Wang et al., Science, Vol. 253, pp. 769–771 (1991); Alfano et al., Physics World, pp. 37–40 (January 1992); and Wist et al., "A Light Imaging Technique for the Improved Detection of Breast Cancer," Eighth Southern Biomedical Engineering Conference, Richmond, Virginia (Oct. 15–16, 1989).

Patents of interest to the present invention include U.S. Pat. No. 5,140,463 to Yoo et al., issuing Aug. 18, 1992 (U.S. Ser. No. 07/489,942, filed Mar. 8, 1990); U.S. Pat. No. 4,945,239 to Wist et al., which issued Jul. 31, 1990; U.S. Pat. No. 4,115,699 to Mizuta et al., which issued Sep. 19, 1978; U.S. Pat. No. 4,515,165 to Carroll, which issued May 7, 1985; U.S. Pat. No. 4,707,128 to Coles, which issued Nov. 17, 1987; U.S. Pat. No. 4,212,306 to Mahmud, which issued Jul. 15, 1980; and U.S. Pat. No. 4,570,638 to Stoddart et al., which issued Feb. 18, 1986.

SUMMARY OF THE INVENTION

It is an object of the present invention to provide a novel technique for imaging an object in or behind a scattering medium.

It is another object of the. present invention to provide a technique as described above that does not require the use of x-rays.

It is still another object of the present invention to provide a technique as described above that may be used in medicine, for example, to detect tumors or the like having a size on the sub-centimeter scale.

To achieve the purpose of the present invention as broadly set forth above, a technique for imaging an object in or behind a scattering medium is provided which comprises the steps of (a) making the object to be detected luminescent, (b) illuminating the object through the scattering medium with a beam of illuminating light, the illuminating light being of a sufficient wavelength to cause the object to luminesce, (c) whereby luminescent light is emitted from the object into the scattering medium, (d) filtering out illuminating light from light emergent from the scattering medium and (e) forming an image of the filtered light.

In a preferred embodiment of the invention, the image quality of the object is further improved by having the scattering medium partially absorb the luminescent light.

As can readily be appreciated, in those instances wherein the object to be detected possesses sufficient native luminescence, no steps need be taken to make the object luminescent.

The present invention is also directed to a system for forming an image of a luminescent object in or behind a scattering medium.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

As discussed above, one way to observe an object in a medium is to illuminate it with a beam of light. The image of the object can then be reconstructed either from the shadow of the object (transillumination) or from the signal light backscattered from the object in the backscatter configuration. Unfortunately, as the illuminating light traverses deeply into the random scattering medium, its signal intensity decreases while the multiple scattered light intensity increases. The signal light contains the image information of the object, while the multiple scattered light contributes noise to the image unless its phase is known. When the light traverses beyond a certain thickness, the object may not be observed because the signal intensity is reduced below the noise level.

In accordance with the teachings of the present invention, a novel way to reduce the amount of noise from the multiple scattered light is to shorten the distance the signal light has to travel in the random medium. Typically, the total distance that the signal light transverses in the medium is the thickness of the medium in the transillumination approach, whereas the distance the signal light travels is twice the depth of the object in the backscattered light viewing direction. A shorter signal distance for the signal light can be accomplished if the object is made luminescent and then viewed from the luminescent light. The distance that the luminescent signal light traverses is from the object to the exit point of the scattering medium, which is shorter than the distance the illuminating signal light had to traverse in either the transillumination or backscattered techniques. Hence, viewing the object in the luminescence spectral range, while filtering out the illuminating light, can result in better image quality in both the transillumination and backscattered configurations.

The quality of the image obtained from a luminescent object in accordance with the teachings of the present invention can be further improved by introducing an absorbing dye into the medium that preferentially absorbs the luminescent light. The underlying physical principle is that the multiple scattered light on the average travels over a longer path length than the ballistic signal. The mean distance that the multiple scattered light travels in the medium is $z^2/l_t$, which is longer than z, the distance the ballistic light transverses through a thickness z, where $l_t$ is the photon transport mean free path. Consequently, the multiple scattered light, which travels over a longer path length, is attenuated more than the signal light by absorption. The image quality of an object should, therefore, be improved when it is viewed in the overlapping spectral region between the luminescence spectrum of the object and the absorption spectrum of the surrounding medium.

Figure 1:
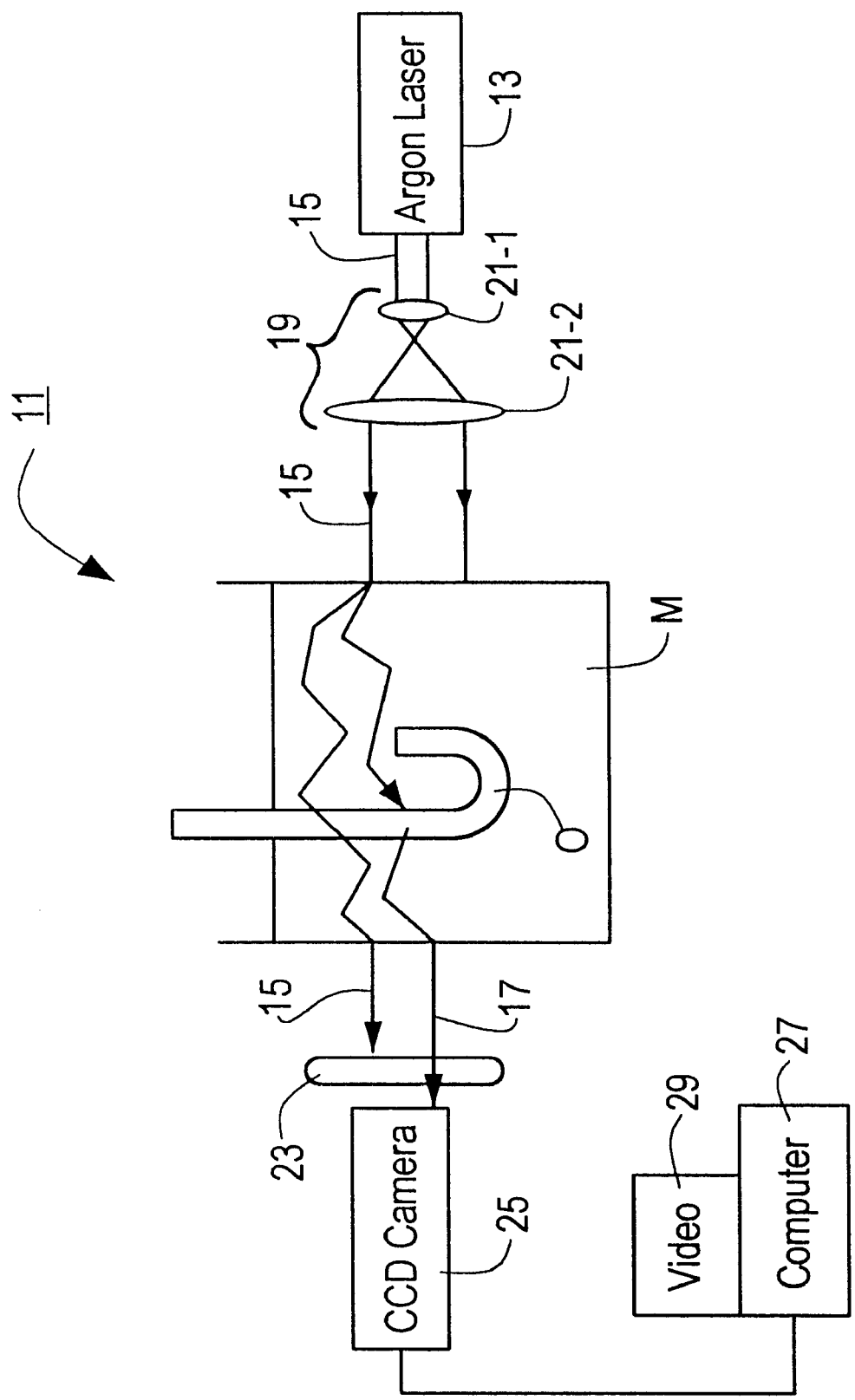
FIG. 1 is a schematic diagram of one embodiment of a system for forming an image of a luminescent object in or behind a scattering medium, the system being constructed according to the teachings of the present invention.

Referring now to FIG. 1, there is shown a schematic diagram of a system for imaging a luminescent object 0 placed in a scattering medium M, the system being constructed according to the teachings of the present invention and represented generally by reference numeral 11.

System 11 includes a light source 13 for generating a beam of illuminating light 15. The wavelength of illuminating light 15 is appropriately chosen so that, when light 15 is incident on luminescent object 0, luminescent light 17 is emitted therefrom. A beam expander 19, made up of a pair of lenses 21-1 and 21-2, is preferably included in system 11 so that a large portion of scattering medium M is illuminated at one time.

A filter 23 for selectively filtering out illuminating light 15 from the light emergent from scattering medium M is placed on the far side of medium M in the transillumination position. A charge coupled device (CCD) camera 25 is placed behind filter 23 for imaging the light transmitted through filter 23, i.e., primarily the luminescent light emitted from object 0. A computer 27 is coupled to CCD camera 25 for recording the image formed by camera 25. A video terminal 29 for displaying, if desired, the image formed by camera 25 is coupled to computer 27.

As can readily be appreciated, system 11 could be arranged in a backscattered geometry by positioning filter 23 and CCD camera 25 on the same side of medium M as light source 13.

EXAMPLES

Figures 2A, 2B, 2C, 2D, 2E:
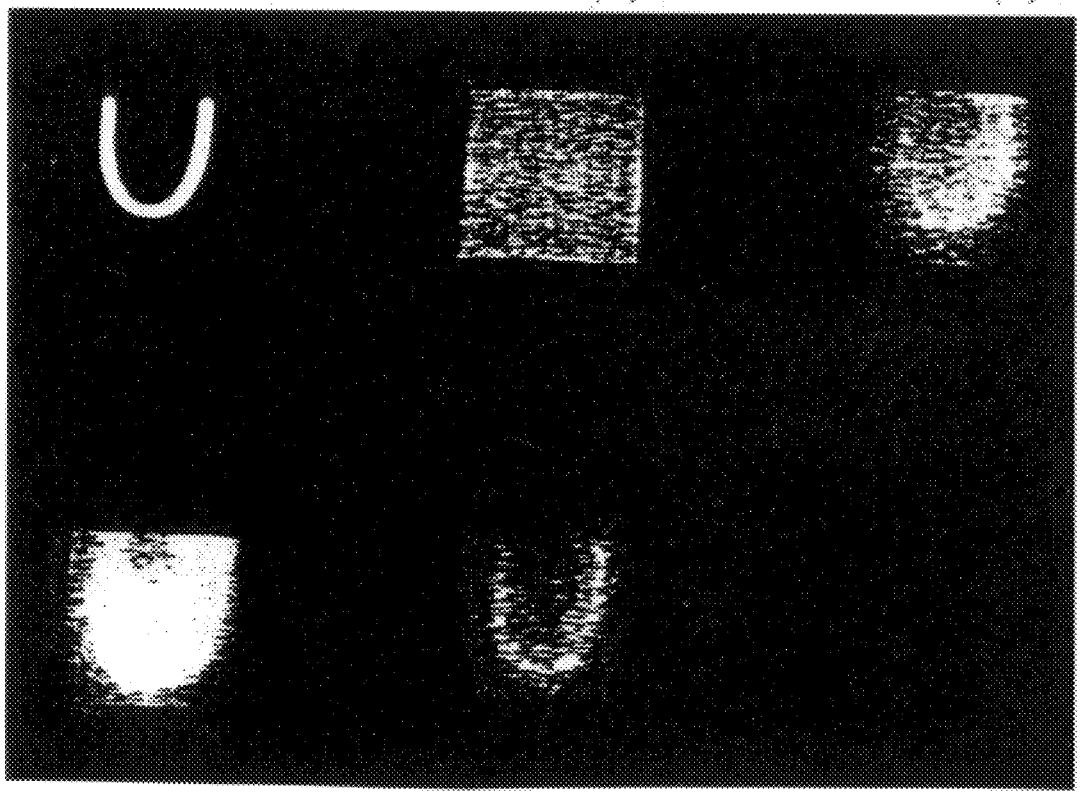
FIGS. 2(a) through 2(e) are images of a U-shaped object placed in a 25 mm thick medium obtained using a CCD camera in the transmission geometry (a) with the object placed in water (i.e., a relatively non-scattering medium); (b) with the object placed in a scattering medium made up of water and latex beads of diameter 0.46 um at a latex concentration of $10 \times 10^{16}$ m$^{-3}$ with both illuminating and luminescent light being detected by the CCD camera; (c) under the same conditions as in (b) except that the illuminating light is filtered out; (d) under the same conditions as in (c) except that the medium is made absorbing by the introduction thereinto of an absorbing dye (malachite green), the absorption length being 1.8 mm; and (e) under the same conditions as in (d) except that additional absorbing dye was added to the medium to make the absorption length 0.9 mm.
Figure 3A:
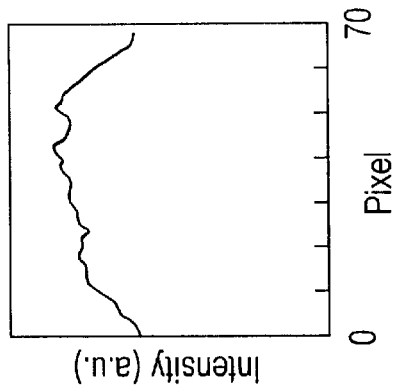
FIGS. 3(a) through 3(e) are graphic representations of the intensity of light across a line in the middle of each of the images in FIGS. 2(a) through 2(e), respectively, with the scale being 0.17 mm/pixel.
Figure 3B:
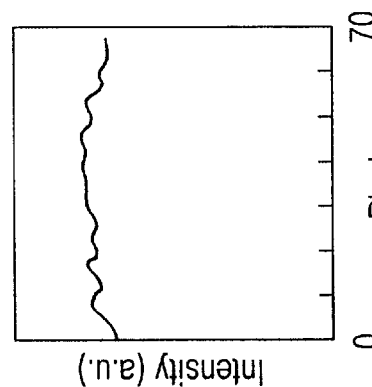
Figure 3C:
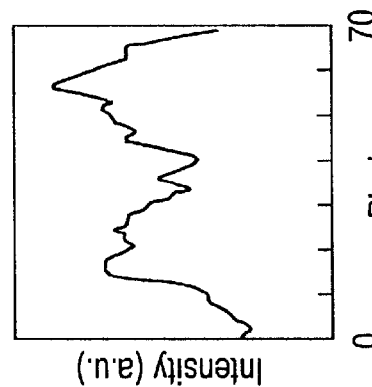
Figure 3D:
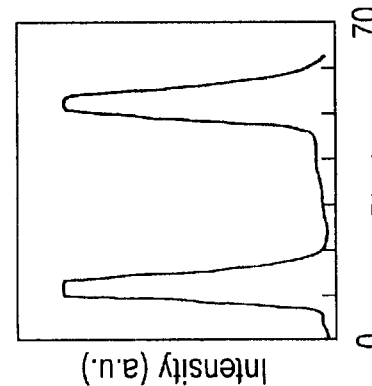
Figure 3E:
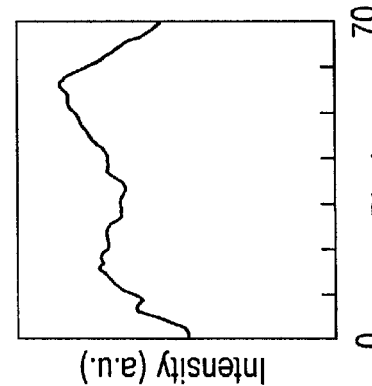

A U-shaped glass tube of 1-mm bore was filled with Rhodamine 640 dye dissolved in ethylene glycol and sealed. The U-shaped tube was then submerged in a glass cell containing clear water with a 25-mm thickness, the tube being positioned 10 mm from the back surface of the glass cell. The object was then illuminated by an argon laser at 488 nm, whereby it fluoresced in the 580–640 nm spectral range. The image of the object was then detected by a charge-coupled-device (CCD) camera in the transmission-mode geometry and recorded by a personal computer. FIG. 2(a) shows the image taken by the CCD camera.

Latex beads of 0.46-um diameter were then added to the water, creating a random scattering medium. As the concentration of the latex beads increased, the image became blurred and disappeared as shown in FIG. 2(b), where the bead concentration is $10 \times 10^{16}$ m$^{-3}$. The blurred image demonstrates that transillumination fails to image the object in this scattering medium even though the object (Rhodamine 640) strongly absorbed the incident beam (the argon laser at 488 nm). The U-shaped object becomes recongizable, as shown in FIG. 2(c), when the illuminating laser light is filtered out but the luminescent light is allowed to pass to the CCD. Corning 1–67 and long-pass 560 nm filters were used and placed in front of the CCD camera to remove the argon laser light and to allow luminescent light above 570 nm to pass through.

The quality of the image was further improved by the addition of an absorbing dye into the random medium that preferentially absorbs the Rhodamine 640 fluorescence. Malachite Green dye was selected for this purpose and was added to the random scattering medium. The image obtained under these conditions is shown in FIG. 2(d), which shows a better image quality compared with that of FIG. 2(c). The absorption length of the scattering medium for FIG. 2(d) was measured to be 1.8 mm at 615 nm. The addition of more Malachite Green further improved the images. The contrast of images shown in FIGS. 2(a) through 2(e) is best illustrated by a plot of the spatial intensity distribution along a horizontal line across the image. The corresponding digitized intensity plots for the images of FIGS. 2(a) through 2(e) are shown in FIGS. 3(a) through 3(e), respectively. The two peaks shown in FIG. 3(a) correspond to the emitted light across the two legs of the U-shaped object. FIG. 2(e) shows the best image contrast in which the absorption is strongest ($l_a$=0.9 mm.).

Figures 4A, 4B, 4C:
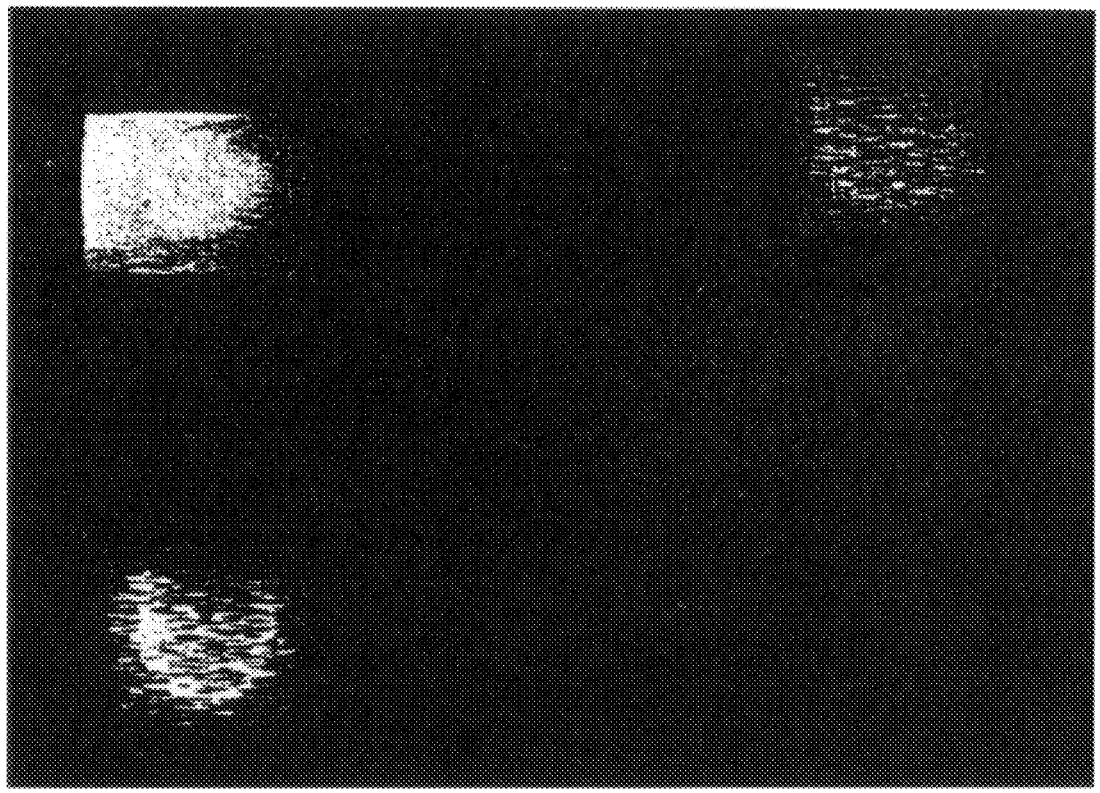
FIGS. 4(a) through 4(c) are images of an object placed 10 mm from the front surface of a scattering medium containing latex beads at a concentration of $8.1 \times 10^{15}$ m$^{-3}$ obtained using a CCD camera in a backscattered geometry (a) with both the illuminating and luminescent light being allowed to pass to the CCD camera; (b) with the illuminating light being filtered out; and (c) under the same conditions as in (b) except that the medium is made absorbing with an absorption length of 0.34 mm.

The image of the object was also studied in the backscattered geometry. As described below, the image quality improved when the fluorescence technique of the present invention was used. The random medium used to demonstrate the improvement obtained by use of the present technique consisted of latex beads at a concentration of $8.1 \times 10^{15} m^{-3}$ suspended in water. The U-shaped object was placed 10 mm from the front surface of the medium. FIG. 4(a) shows that the object is not recognizable when there was no filter to remove the scattered illuminating light from the CCD camera. The CCD camera detected the multiple backscattered noise of the illuminating light, which is more intense than that in the transmission geometry. When this multiple scattered light was removed by placing a filter (long-pass 560 nm) in front of the CCD, a slightly recognizable U-shaped image was observed, as shown in FIG. 4(b). When absorption is introduced into the random medium, the quality of the image improves, as shown in FIG. 4(c), where the absorption length is 0.5 mm at 615 nm.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for imaging an object in or behind a scattering medium comprising the steps of:
   (a) making the object to be detected luminescent;
   (b) illuminating the object through the scattering medium with a beam of illuminating light, the illuminating light being of a sufficient wavelength to cause the object to luminesce;
   (c) whereby luminescent light is emitted from the object into the scattering medium, the luminescent light comprising a ballistic component and a multiple scattered component;
   (d) making the scattering medium preferentially absorbing of the luminescent light emitted by the object so that the multiple scattered component of the luminescent light is preferentially absorbed by the scattering medium as compared to the ballistic component of the luminescent light;
   (e) filtering out illuminating light from light emergent from the scattering medium; and
   (f) forming an image of the filtered light.

2. The method as claimed in claim 1 wherein said luminescent making step comprises selectively adding a fluorescent dye to the object.

3. The method as claimed in claim 1 wherein the object is located in the scattering medium and wherein said filtering out step is performed on light emergent from the scattering medium in a transmission geometry.

4. The method as claimed in claim 1 wherein the object is located in or behind the scattering medium and wherein said filtering out step is performed on light emergent from the scattering medium in a backscattered geometry.

5. The method as claimed in claim 1 further comprising the steps of recording and/or displaying the image formed of the filtered light.

6. A system for imaging a luminescent object in or behind a scattering medium, said system comprising:
   (a) means for illuminating the luminescent object through the scattering medium with a beam of illuminating light, the illuminating light being of a sufficient wavelength to cause the luminescent object to luminesce;
   (b) whereby luminescent light is emitted from the luminescent object into the scattering medium, the luminescent light comprising a ballistic component and a multiple scattered component;
   (c) means added to the scattering medium for making the scattering medium preferentially absorbing of the luminescent light emitted by the object so that the multiple scattered component of the luminescent light is preferentially absorbed by the scattering medium as compared to the ballistic component of the luminescent light;
   (d) means for filtering out illuminating light from light emergent from the scattering medium; and
   (e) means for forming an image of the filtered light.

7. A method for imaging a luminescent object in or behind a scattering medium comprising the steps of:
   (a) illuminating the luminescent object through the scattering medium with a beam of illuminating light, the illuminating light being of a sufficient wavelength to cause the luminescent object to luminesce;
   (b) whereby luminescent light is emitted from the luminescent object into the scattering medium, the luminescent light comprising a ballistic component and a multiple scattered component;
   (c) making the scattering medium preferentially absorbing of the luminescent light emitted by the object so that the multiple scattered component of the luminescent light is preferentially absorbed by the scattering medium as compared to the ballistic component of the luminescent light; and
   (d) forming an image of the light emergent from the scattering medium, said image being devoid of illuminating light.

* * * * *